United States Patent
Stofman et al.

(10) Patent No.: US 10,117,863 B2
(45) Date of Patent: Nov. 6, 2018

(54) METHODS AND COMPOSITIONS FOR ENHANCING FEMALE SEXUAL AROUSAL AND TREATING FEMALE SEXUAL DYSFUNCTION

(71) Applicants: Guy M. Stofman, Pittsburgh, PA (US); Michael J. Pelekanos, Murrysville, PA (US)

(72) Inventors: Guy M. Stofman, Pittsburgh, PA (US); Michael J. Pelekanos, Murrysville, PA (US)

(73) Assignee: Life Science Enhancement Corporation, Pittsburgh, PA (US)

( * ) Notice: Subject to any disclaimer, the term of this patent is extended or adjusted under 35 U.S.C. 154(b) by 0 days.

(21) Appl. No.: 14/927,902

(22) Filed: Oct. 30, 2015

(65) Prior Publication Data

US 2017/0119749 A1    May 4, 2017

Related U.S. Application Data

(63) Continuation of application No. 13/640,518, filed as application No. PCT/US2011/032652 on Apr. 15, 2011, now abandoned.

(60) Provisional application No. 61/324,354, filed on Apr. 15, 2010.

(51) Int. Cl.
| | |
|---|---|
| *A61K 31/34* | (2006.01) |
| *A61K 31/44* | (2006.01) |
| *A61K 31/455* | (2006.01) |
| *A61K 31/198* | (2006.01) |
| *A61K 9/00* | (2006.01) |
| *A61K 31/375* | (2006.01) |

(52) U.S. Cl.
CPC ......... *A61K 31/455* (2013.01); *A61K 9/0034* (2013.01); *A61K 31/198* (2013.01); *A61K 31/375* (2013.01)

(58) Field of Classification Search
CPC .. A61K 31/198; A61K 31/44; A61K 31/4406; A61K 31/375
USPC ........................ 514/355, 356, 474
See application file for complete search history.

(56) References Cited

FOREIGN PATENT DOCUMENTS

| | | | |
|---|---|---|---|
| RU | 2013088 C1 | * 5/1994 | |
| WO | WO 2011130608 A1 | * 10/2011 | ........... A61K 31/198 |

OTHER PUBLICATIONS

Russian Patent No. 2013088 C1 (1994), English translation.*

* cited by examiner

*Primary Examiner* — Kevin E Weddington
(74) *Attorney, Agent, or Firm* — Dureska & Moore, LLC; Brent L. Moore; David J. Danko

(57) ABSTRACT

Methods and compositions for enhancing female sexual arousal and treating female sexual dysfunction utilize L-arginine or equivalents and/or derivatives thereof, and an agent that enhances the activity of the L-arginine or equivalent thereof. These enhancing agents include niacin and/or nicotinamide. Niacin and/or nicotinamide, in combination with L-arginine or its equivalent allow a desired amount of nitric oxide to be delivered or generated at the female genitals in order to increase vasodilation and blood flow to the area to enhance sexual arousal and/or pleasure and to treat sexual dysfunction.

4 Claims, No Drawings

METHODS AND COMPOSITIONS FOR ENHANCING FEMALE SEXUAL AROUSAL AND TREATING FEMALE SEXUAL DYSFUNCTION

CROSS-REFERENCE TO RELATED APPLICATION

This application is a continuation of U.S. application Ser. No. 13/640,518 filed on Jan. 2, 2013, which claims the benefit of PCT application Serial No. PCT/US2011/032652 filed on Apr. 15, 2011, which claims the benefit of U.S. Provisional Patent Application Ser. No. 61/324,354, filed Apr. 15, 2010, all of which are hereby incorporated by reference in their entirety.

BACKGROUND OF THE INVENTION

Field of the Invention

Embodiments of the invention relate generally to methods and compositions useful in enhancing female sexual arousal and for treating female sexual dysfunction. A preferred embodiment of the invention is directed to methods and compositions that utilize L-arginine or equivalents and/or derivatives thereof, and an agent that enhances the activity of the L-arginine or equivalent thereof. Such agents include niacin and nicotinamide. Not wishing to be bound by theory, it is believed that niacin and nicotinamide may function as agonists of Nitric Oxide Synthase ("NOS"). Accordingly, niacin and/or nicotinamide, in combination with arginine or its equivalent will allow a desired amount of nitric oxide ("NO") to be delivered or generated at the female genitals in order to enhance sexual arousal and/or sexual pleasure and to treat sexual dysfunction.

Background Art

The female sexual experience is a complex phenomenon heavily influenced by emotional, psychological, relational, and physical modalities. Each individual female has specific needs and desires that involve all of the above or anyone factor at any given moment. Both sexual arousal and/or sexual pleasure are components of the female sexual experience.

Sexual dysfunction is also a complex and amorphous concept, but can refer to the failure to achieve anyone of the four phases of sexual response—appetite, excitement, orgasm, or resolution.

While prevalence of male sexual dysfunction is often cited in research and addressed by various pharmaceutical products, female sexual dysfunction ("FSD") has been largely ignored. According to a 1999 report in the Journal of the American Medical Association, 43% of women suffer from FSD, significantly higher than the 31% prevalence of sexual dysfunction in men. It is difficult to effectively evaluate the female sexual response due to the complex emotional, relational, and physical variables that are associated with each encounter. Religious and cultural influences also play a role in the attitudes towards sex and this can complicate the sexual response as well. Despite the prevalence of women suffering from the condition, no FDA approved pharmaceutical treatment has been developed. In 2004, the FDA rejected fast-track approval of Proctor & Gamble's Intrinsa transdermal system (skin patch), a product aimed at decreasing FSD in surgically menopausal women, demonstrating the difficulty and expense in addressing concerns of safety and efficacy of drug therapy in this market. A recent study of 256 women using a topical botanical product called Zestra® demonstrated a favorable sexual response after topical application, but 14% displayed mild to moderate burning (Ferguson, D. M., 2010, Randomized placebo-controlled double-blind, parallel design trial of the efficacy and safety of Zestra® in women with mixed desire/interest/arousal/orgasm disorders, J. of Sex and Marital Therapy, 36:66-86).

DESCRIPTION OF THE INVENTION

The present invention relates to compositions and methods for using compositions to treat female sexual dysfunction or to enhance the female sexual experience. The methods generally employ administering to the genitals of the patient being treated a composition comprising a NO donor or producer in conjunction with an agonist of NOS. More specifically, the NO donor is L-arginine or equivalents and/or derivatives thereof, and the NOS agonist is niacin or nicotinamide. As will be appreciated, it is believed these compounds generate NO in vivo; and the compounds combined may result in a synergistic amount of NO being delivered to the clitoris as compared to either agent administered alone.

The present invention is directed to methods for enhancing female sexual arousal and/or sexual pleasure and for treating female sexual dysfunction in a patient comprising topically administering to the genitals of the patient an effective amount of L-arginine or equivalents and/or derivatives of L-arginine and an NOS agonist. The NOS agonist in the present application may be either niacin or nicotinamide (or both). In addition, the present invention may include an anti-oxidant to reduce the effect of free radicals that may be produced as a result of the combination or application of these ingredients.

The term "sexual dysfunction" is used herein in its broadest sense, but applies mainly to female sexual dysfunction. In females, sexual dysfunction refers, for example, to pain or discomfort during sexual intercourse, diminished vaginal lubrication, delayed vaginal engorgement, increased time for arousal, diminished ability to reach orgasm, and/or diminished clitoral sensation.

It will be appreciated that an aspect of the present invention is the enhancement of sexual pleasure and stimulation or arousal. For example, an orgasmic woman seeking a more pronounced sexual response can be treated according to the present methods. A more pronounced sexual response or enhancement of sexual pleasure includes, but is not limited to, decrease in the amount of foreplay, decrease in the period between orgasms, decrease in the intercourse time required for orgasm, and achievement of multiple orgasms, as well as more intense orgasms.

The term "patient" as used herein refers generally to female members of the animal kingdom. Because the present methods include inducement of sexual stimulation, they have application in, for example, animal husbandry. The present methods are therefore not limited to applications for humans.

As noted, the active ingredients of the present invention are topically administered to the genitals of the patient. Female genitals to which the present compositions can be administered include the vagina, clitoris, mons pubis, clitoral hood, labium anterium, labium posterius, labia majora, and labia minora, hymen, prepuce of the clitoris, vestibule of the vagina, and/or vestibular glands.

L-arginine is a natural amino acid that is widely commercially available. Equivalents of L-arginine are known in the art and include any agent that enhances the bioavailability of L-arginine. As examples, L-citrulline (a precursor of L-arginine) and arginase inhibitors are included in the term L-arginine equivalents.

An embodiment of the present invention is L-citrulline in combination with niacin or nicotinamide for sexual enhancement. L-citrulline is an amino acid that is known generally to support the body in optimizing blood flow through its conversion to L-arginine and then NO. More particularly, L-citrulline is a precursor to the formation of L-arginine and is known to play a role in arginine recycling, which is an important factor in NO release.

The L-arginine or equivalents and/or derivatives of L-arginine used according to the present invention generate NO. As noted above, NO causes vasodilation, which results in increased blood flow to the area in which the vasodilation is effected. Increased blood flow to the erectile tissue of females serves to treat the sexual dysfunction. For example, application of the present compositions to the clitoris and/or clitoral hood of the female results in increased blood supply leading to engorgement of the clitoris. This serves to heighten sexual arousal, enhance sexual pleasure, and otherwise minimize if not eradicate the symptoms associated with sexual dysfunction. Application of the present compositions to the vagina and external genitalia also results in lubrication sufficient so as to allow pain-free sexual intercourse.

It has been found that utilization of L-arginine in combination with niacin and/or nicotinamide results in increased clitoral blood flow. It is believed that these agents are functioning as NOS agonists. Generation of NO and the vasodilation that occurs as a result can also ultimately lead to the generation of superoxide molecules. Superoxide molecules can combine with NO to produce peroxynitrite. The detrimental effects of this reaction are two-fold: the reaction ties up NO, and therefore minimizes the amount of NO available for vasodilation; and the generation of peroxynitrite may cause tissue and cellular damage. Therefore, an embodiment of the present invention may be (i) arginine or its equivalent; (ii) niacin and/or nicotinamide; and/or (iii) an anti-oxidant. A preferred antioxidant is L-ascorbate, also known as ascorbic acid or vitamin C, and derivatives thereof. Derivatives of vitamin C such as ester C (the calcium salt of L-ascorbate), dehydro-L-ascorbate, (the oxidized derivative of vitamin C), or ester C of dehydro-L-ascorbate can also be used, as can lapidated derivatives such as ascorbic acid palmitate; these compounds are collectively referred to herein as vitamin C derivatives or ascorbic acid derivatives.

The antioxidants according to the present methods and compositions are preferably used in supratherapeutic amounts, that is, the amount necessary to control peroxynitrite formation. Thus, the antioxidant is not used in trace amounts to prevent oxidation of the composition itself or to extend the shelf life of the composition, although it also serves that function; the antioxidant itself contributes to the therapeutic benefit realized by the patient.

As a result of the vast number of females in this country that may benefit by an enhancement of their sexual experience, a topical cream was formulated that has the ability to cause local, non-systemic vasodilation to the areas applied (in this instance the clitoral hood). This localized vasodilation leads to clitoral engorgement that has the potential to enhance the sexual experience when stimulated. The goal was to develop a topical cream that would enhance the sexual experience in randomized selected sexually active females.

Compositions comprising L-arginine, niacin and nicotinamide can be produced and used in accordance with the present invention that are useful to treat or affect the female sexual function. For example, the present invention relates to compositions, preferably for topical or local use, which comprise one or more of the following ingredients, including, but not limited to, L-arginine, niacin and nicotinamide. The compositions can produce one or more of the following pharmacological effects, including, but not limited to, increases in localized nitric oxide, cAMP production and/or elevation, cGMP production and/or elevation, prostaglandin D2 production, inhibition of prostaglandin D2 breakdown, calcium channel antagonism, phosphodiesterase inhibition, anti-oxidation, vasodilation, and smooth muscle relaxation.

A useful composition in accordance with the present invention can comprise L-arginine. L-arginine can be prepared by any suitable method. L-arginine can be present in a composition of the present invention in any effective amount, e.g., 1-100%, 10-95%, 20-95%, 30-95%, 50-95%, 70-90%, 60-90%, 20%, 21%, 22%, 23%, 24%, 25%, 26%, 27%, 28% 29% 30%, etc., w/w (i.e., weight of ingredient/weight of total composition).

An effective amount of each of the L-arginine or equivalents and/or derivatives thereof; a NOS agonist; and/or the antioxidant should be used. The effective amount can be that amount of the present composition necessary to bring about the desired amount of blood flow to the erectile tissue. "Erectile tissue" refers to the erectile tissue of the clitoris. The amount used should cause blood engorgement without significantly modifying motor or sensory functions. An effective amount can also be that amount needed to alleviate one or more of the symptoms of sexual dysfunction or to enhance sexual arousal or sexual pleasure. Alleviating the symptoms of sexual dysfunction denotes a decrease in the inhibition of one or more of the four phases of sexual response noted above (appetite, excitement, orgasm or resolution). Such alleviation is manifested by, for example, increasing sexual desire, enhancing the ability to achieve and maintain an erection, enhancing the ability to ejaculate, enhancing the ability to experience orgasm for females, and promoting vaginal lubrication A composition of the present invention can also comprise niacin. Niacin can be prepared by any suitable method. Niacin can be present in a composition of the present invention in any effective amount, e.g., 0.01-100%, 0.01-1%, 0.05-2%, 0.09%-3%, 2%-5%, 0.05%, 0.06%, 0.07%, 0.08%, 0.09%, 0.1%, 0.11%, 0.12%, 0.13%, 0.14%, 0.15% etc., w/w.

A composition of the present invention can also comprise nicotinamide. Nicotinamide can be prepared by any suitable method. Nicotinamide can be present in a composition of the present invention in any effective amount, e.g. 0.001-100%, 0.001-1%, 0.005-0.2%, 0.09%-3%, 2%-5%, 0.005%, 0.006%, 0.007%, 0.008%, 0.009%, 0.01%, 0.011%, 0.012%, 0.013%, 0.014%, 0.015% etc., w/w.

The effective amount will vary depending on various factors including the patient to be treated, the sex of the patient, the sexual dysfunction being treated, the severity of the dysfunction, the patient's age and reaction to the treatment, the particular formulation employed, and the like. The determination as to what is an effective amount for each patient is within the skill of those practicing in the art.

An aspect of the present invention is topically-applied cream made of topical ingredients generally recognized as safe ("GRAS") or agents which are well understood to be safe and tolerable, such as Arginine Hydrochloride USP, Niacinamide Powder, Niacin USP (Vitamin B3), Pentylene Glycol (GRAS) used commonly as an emulsifier, base Emulsifix (GRAS) another common emulsifier used in compounding, and base Lipoderm®, another (GRAS) carrier used for transcutaneous, transmembrane transport of topical medications. It should be noted that the Lipoderm® carrier enhances transport of the active ingredients of the present invention across mucous membranes. The placebo intended to be used in the clinical trials is Lipoderm® only.

In addition to the above-mentioned pharmacological agents, or as an alternative thereof, a composition of the present invention can comprise any agent which possesses one of more of the biological activities associated with said pharmacological agents.

The present invention is preferably delivered in a topical application. It has therefore been discovered that an effective therapeutic level of an NO producer and an antioxidant can be administered topically to the female genitalia, and transdermally delivered through the skin. Thus the present invention allows for the localized delivery of an NO producer while at the same time minimizing, if not eliminating, the tissue and cellular damage that normally accompanies NO production.

The compositions according to the present invention can also include any of various other excipients, such as surfactants, suspending agents, emulsifiers, osmotic enhancers, extenders and dilutants, pH modifiers, fragrances, colors, flavors, and other additives. For example, a surfactant can be used to enhance the bioavailability of the active ingredients by reducing the tension between these ingredients and the skin of the genitals. Humectants and emollients can also be used, as can absorption or penetration enhancers or other additives commonly used in topical vehicles. Examples of suitable absorption enhancers include dimethylsulfoxide ("DMSO") or its analogues, monoalkyl phosphates and pharmaceutically acceptable salts thereof, polyhydroxyesters, long chain fatty acids, polyhydroxyl alcohols and turpenes. The inactive ingredients in the present compositions should be chemically compatible with the active ingredients and should be of a low irritation potential so as not to irritate the genital area.

The active ingredients for the present composition are preferably contained in a pharmaceutical vehicle or carrier suitable for application to the genitals. It will be appreciated that not all pharmaceutical carriers are appropriate for application to this sensitive region. The active ingredients are therefore preferably contained in a pharmacologically inert excipient, such as those reported in the "Remington Pharmaceutical Sciences Handbook", which will be familiar to those skilled in the art. The composition should be prepared in any administration form that is suitable for topical and epimucosal application to the body and on skin that is particularly thin and sensitive. For example, the pharmaceutical carrier can be a composition which facilitates application of the NO donor and antioxidant. One such carrier is methylcellulose, such as that sold commercially under the name K-y® Jelly. Preferably, the carrier has a near neutral pH. Other examples of suitable carriers include water, silicone, waxes, polyethylene glycol, propylene glycol and sugars, and bases containing white petrolatum, paraffin wax, caprylic diglyceryl succinate, diisopropyl adipate and ethoxydiglycol. The composition can be in numerous forms including gels, ointment, foam, spray, cream, salve, lotion, liquid, emulsions, liposomal solution and other forms prepared by methods known in the art. Preferably, the composition has a viscosity such that it will stay generally on the area to which it is applied. A preferred method of delivery is a liposomal solution. Liposomal solutions can be made using commercially available kits following the manufacturer's instructions and with reference to common practices known in the art such as those discussed in "The National Formulary" or "Remingtons Pharmaceutical Sciences Handbook." A pluronic lecithin organogel ("PLO") liposomal solution has been found to be particularly suitable. Compositions can be administered in any form by any effective route, including, e.g., oral, parenteral, enteral, intraperitoneal, topical, local, dermal, transdermal, ophthalmic, nasally, nasopharyngeal absorption, local, topical, non-oral, aerosol, inhalation, subcutaneous, intramuscular, buccal, sublingual, rectal, vaginal, intra-arterial, rapid infusion, intravenously, long-release implants, etc. In general, any delivery means, including devices, polymers, etc., that are used to deliver agents vaginally can be utilized in accordance with the present invention, such as means for delivering antiviral agents, bacteriocides, contraceptives, hormones, spermicides, virucides, lubricants, etc. While "donor" and "antioxidant" and the like are used in the singular, that more than one NO donor and more than one antioxidant can be used in the present methods and compositions.

In preferred embodiments of the invention, compositions are administered to the external female genitalia and/or vaginally, e.g., as a vaginal cream, foam, gel, jelly, liquid, emulsion, solution, suspension, cream, spray, powder, suppository, tablet, device, etc. For example, a composition can be preferably applied to the female external genitalia, such as the mons pubis, labia majora and minora, hymen, clitoris, prepuce of the clitoris, vestibule of the vagina, and/or vestibular glands.

EXAMPLES

The following examples are intended to illustrate the present invention, and should not be construed as limiting the invention in any way.

Example 1

Methods: A large number of randomly selected sexually active females are to be chosen prospectively to participate in this placebo run, blinded study. To be, eligible to participate the women must have been sexually "experienced" in arousal/orgasm, with a desire for the sexual experience. Those who were excluded were females with sexual pain disorders, psychological sexual aversion disorders, vaginismus, pregnant/nursing, diabetes mellitus, central nervous system disorders, psychosis, or any other condition that the clinician determined may affect the responder to sign informed consent or adequately measure their sexual response.

The women are to be counseled on the first visit as to protocol that consisted of informed consent, instructions on topical application of "formula" (active ingredient), and placebo, and directions on sexual activity. The women chosen are to be preferably engaged in some type of sexual activity either by spousal interaction or masturbation at least once a week and are able to record their experience by answering a standard "Female Intervention Efficacy Index" ("FIEI") questionnaire developed by Berman and Berman (Pauls, Rachel N. et al. "Female Sexual Dysfunction: Principles of Diagnosis and Therapy." Obstetrical & Gynecological Survey. March 2005; 60:3 pp. 196-205), which is well known in the art, to measure the immediate response; a sample of which is attached as Exhibit A. The women are to be asked to apply the cream, wait approximately 5-10 minutes, and then engage in some form of sexual activity.

The women are asked to respond to the survey within 12 hours of the encounter and compare the response to each of two preparations (one active, one placebo) that they were blinded to. Two "cycles" of activity are necessary to complete the study. Follow up is to be conducted by standard FIEI questionnaire and is to be mailed back to the principal clinical investigators. Participants will be asked to comment on their experience as well. Responses will be collated and analyzed for statistical significance. Any patient who for whatever reason could not meet the criteria as set will be excluded in the study and replaced randomly to get to 100 patients.

Discussion: The female sexual experience is a complex phenomenon heavily influenced by emotional, psychological, relational, and physical modalities. Be that as it may, each individual woman has specific needs and desires that involve all of the above or anyone factor on any given moment. The present invention is directed to being able to generally enhance the female sexual experience. It is well documented that L-arginine as it breaks down to NO is a potent vasodilator. With the addition of Niacin (Vitamin B3), in itself a vasodilator with Nicotinamide, a metabolite of niacin, a desirable response is obtained that is well tolerated to the mucous membranes. In the study of 100 patients it is expected that the topical cream will be well tolerated with few complaints of burning or discomfort. The lipoderm transmembrane carrier allows effective delivery of the active ingredients and in itself is well tolerated.

There are a number of reliable sexual indices that measure outcomes of sexual function. The Derogatis Sexual Functioning Inventory ("DSFI"), the Brief Index of Sexual functioning for Women ("BISF-W"), and the Index of Female Sexual Function ("IFSF"). As Berman and Berman noted, the "standard" sexual response indexes seem to evaluate "global measurements of sexual function, evaluation of long term improvements" (Pauls, Rachel N. et al. "Female Sexual Dysfunction: Principles of Diagnosis and Therapy." Obstetrical & Gynecological Survey. March 2005; 60:3 pp. 196-205). Since sexual urges are often immediate and spontaneous, of particular interest were the immediate response outcomes of the sexual experience. It is felt that if the immediate sexual experience can be improved by increasing blood flow to the vaginal vault that will subsequently increase vaginal lubrication, the long-term consequences will lead to a better sexual life. Because of this, the FIEI was chosen as an immediate outcome measure of the effects of the present invention on the female sexual response.

Example 2

Preparation of a Cream for Topical Application

A composition was formulated comprising 20% w/w arginine hydrochloride USP, 0.01% w/w nicotinamide (niacinamide), and 0.1% niacin USP (nicotinic acid).

0.1 mg niacinamide was triturated in 1.0 mg lipoderm and combined with 22 g Arginine hydrochloride USP, 0.11 g niacin USP (nicotinic acid) and triturated using geometric dilution in a wedge wood mortar. Powders were wetted with 10.01 ml petylene glycol after which 2.2 g PCCA Emulsifix™-205 and 110 g PCCA lipoderm® was added to the mixture. The formulation was mixed, passed through an ointment mill and mixed again. The formulation was dispensed into an ointment jar.

Example 3

Preparation of a Cream for Topical Application

A composition was formulated comprising 30% w/w arginine hydrochloride USP, 0.01% w/w nicotinamide (niacinamide), and 0.1% niacin USP (nicotinic acid).

0.125 mg niacinamide was combined with 37.5 g Arginine hydrochloride USP, 1.25 g niacin USP (nicotinic acid), 0.125 g ascorbyl palmitate, 11.375 ml petylene glycol, 2.5 g PCCA Emulsifix™-205, 1.375 ml glycerin USP and 125 g PCCA lipoderm®.

Example 4

A composition comprising 30% L-arginine, 0.01% niacinamide, 0.1% niacin was applied to the clitoris of a 52 year old female and clitoral blood flow was quantitatively measured with Doppler plethismography. Compared with a placebo composition lacking the active ingredients (Baseline measurement), clitoral blood flow more than doubled ten minutes after application of the composition. Each treatment was conducted on separate days as excess stimulation with the Doppler probe can, in and of itself increase clitoral blood flow.

As evidenced by the above examples, the present methods and compositions are effective in enhancing sexual arousal and/or sexual pleasure and treating sexual dysfunction.

Whereas particular embodiments of this invention have been described above for purposes of illustration, it will be evident to those skilled in the art that numerous variations of the details of the present invention may be made without departing from the invention as defined in the appended claims.

What is claimed is:

1. A composition comprising: an effective amount of L-arginine, an effective amount of niacin, an effective amount of nicotinamide, and an anti-oxidant comprising at least one of ascorbic ester C, dehydro-L-ascorbate, ester C of dehydro-L-ascorbate, ascorbic acid palmitate.

2. The composition of claim 1 wherein the concentration of L-arginine is about 15% to about 45% w/w.

3. The composition of claim 1 wherein the concentration of niacin is about 0.05% to 0.5% w/w.

4. The composition of claim 1 wherein the concentration of nicotinamide is about 0.005% to 0.05% w/w.

* * * * *